United States Patent [19]

Lichte et al.

[11] Patent Number: 5,087,250
[45] Date of Patent: Feb. 11, 1992

[54] AUTOTRANSFUSION UNIT WITH VACUUM REGULATION AND CARDIOTOMY RESERVOIR

[75] Inventors: Leo J. Lichte, Riverside; Jack W. Brown, Santa Ana, both of Calif.

[73] Assignee: Gish Biomedical, Inc., Santa Ana, Calif.

[21] Appl. No.: 481,861

[22] Filed: Feb. 16, 1990

Related U.S. Application Data

[63] Continuation of Ser. No. 224,307, Jul. 26, 1988, abandoned.

[51] Int. Cl.$^5$ .............................. A61M 1/00
[52] U.S. Cl. ......................... 604/321; 604/319; 604/4
[58] Field of Search ................... 604/319–321, 604/4–6

[56] References Cited

U.S. PATENT DOCUMENTS

| | | | |
|---|---|---|---|
| 3,783,870 | 1/1974 | Schachet | 604/321 |
| 3,891,416 | 6/1975 | Leonard et al. | 604/317 X |
| 4,437,472 | 3/1984 | Naftulin | 604/320 X |
| 4,439,190 | 3/1984 | Protzmann et al. | 604/319 |
| 4,781,707 | 11/1988 | Boehringer et al. | 604/319 X |
| 4,838,872 | 6/1989 | Sherlock | 604/319 |
| 4,846,800 | 7/1989 | Ouriel et al. | 604/319 X |
| 4,923,438 | 5/1990 | Vasconcellos et al. | 604/319 X |

*Primary Examiner*—Randall L. Green
*Assistant Examiner*—David H. Willse
*Attorney, Agent, or Firm*—George F. Bethel; Patience K. Bethel

[57] ABSTRACT

The disclosure herein sets forth a pleural drainage/autotransfusion unit in combination with a cardiotomy reservoir having a vacuum regulating chamber in connected relationship to the pleural drainage/autotransfusion unit. The vacuum regulating chamber is formed of a portion of said cardiotomy reservoir unit and extends along the axial direction of the reservoir of the autotransfusion unit and can be connected to a source of vacuum. A water seal is interposed between the vacuum regulating chamber and the interior of the reservoir in order to provide for water sealed negative pressure within the reservoir. The function of the cardiotomy reservoir and the pleural drainage/autotransfusion unit can be changed by means of connections that have spring loaded tangs that engage a flange of a barbed inlet port. The connection is sealed by means of a resilient plastic material engaging the barbed inlet ports and can be readily removed therefrom and sealed without the requirement of sealing a tube which has been shrunken over the barbs of the inlet port.

16 Claims, 5 Drawing Sheets

AUTOTRANSFUSION UNIT WITH VACUUM REGULATION AND CARDIOTOMY RESERVOIR

This is a continuation of application Ser. No. 07/224,307, filed July 26, 1988, now abandoned.

FIELD OF THE INVENTION

The field of this invention pertains to surgical apparatus. More particularly, it lies within the field of surgical apparatus for use in open-heart and chest cavity surgery. Such surgery can be performed utilizing oxygenators and certain reservoirs, as well as post operative devices for the patient. This invention pertains to such operation and post operative devices.

BACKGROUND OF THE INVENTION

This invention is an improved unit having cardiotomy reservoir capabilities as well as pleural drainage and autotransfusion capabilities with a vacuum regulation and seal system. It incorporates features pertaining to a quick disconnect for changing the functions of the combined unit hereof. When referring to autotransfusion it should be understood that pleural drainage is incorporated in such activity. Thus, the term pleural drainage/autotransfusion shall refer to when the device or function incorporates pleural drainage by itself or when used with autotransfusion.

Cardiotomy reservoirs have been known in the prior art. Such cardiotomy reservoirs are utilized to retain (store) fluids during open heart surgery from the chest cavity. When fluids are removed from the chest cavity, they are suctioned into the cardiotomy reservoir. Such cardiotomy reservoirs can maintain the fluid in situ therein or filter it. Oftentimes, filtration depending upon the surgical procedure, is a preferred combined function for the cardiotomy reservoir.

Such filtering can remove clots and extraneous material from the blood so that the blood can be returned to the patient. During the passage of the fluid to the patient, it can be through an oxygenator. Oxygenators are well known in the prior art for oxygenating blood in a continuous cycle. Such oxygenators provide the function of the lungs during open heart surgery, so that the blood can be utilized by the body.

The cardiotomy reservoirs of the prior art have also been known to have the filtration system as an option or in some cases been eliminated. In these instances, the blood as passed through the patient is of sufficient purity so as to not require filtering. In some cases a separate filter can be used or an oxygenator can be used to avoid the use of filtration. Be that as it may, the cardiotomy reservoirs are currently an important and helpful adjunct to all apparatus during open-heart surgery.

An innovation of recent note has been the re-introduction of systems for providing autotransfusion. Autotransfusion is the transfusion of the blood lost by a patient back to the patient. Autotransfusion was known as early as the 19th century as the method of recovering a patient's blood. Also, there are known uses of autotransfusion in the literature as early as 1924 on a sophisticated and well thought-out basis. With the advent of blood banks, autotransfusion was not deemed as necessary. The preferred method during a substantial portion of this century was to utilize banked blood.

Such banked blood, although helpful in operations, is not preferable when considering the physiological benefits of utilizing the patient's own blood. Not only does the patient's blood have compatibility when handled properly, but it can be of superior quality to banked blood. This being the case, many surgeons are utilizing techniques of autotransfusion to enhance a patient's overall health during operations.

Autotransfusion techniques are such wherein they rely upon the removal of blood and fluids from a patient's body. The blood is then returned through the autotransfusion unit.

A substantial example of usage is within the open-heart surgical area. Such open-heart surgical usage usually relies upon the withdrawal of fluids from a patient's chest cavity. The withdrawal of fluids is to not only drain the chest cavity of any blood loss, but also other fluids which are drained out of a patient's chest post operatively. Such fluids during autotransfusion are drawn into the autotransfusion unit under vacuum and gravity drain. The source of vacuum has generally been provided by a hospital fixed vacuum system. The vacuum system can incorporate a regulator for purposes of maintaining approximately 20 CM. $H_2O$ vacuum. The 20 CM. $H_2O$ vacuum allows chest drainage to continue on a basis which is not detrimental yet at the same time maintains sufficient draw to pull fluids into the autotransfusion unit and maintain negative pressure in the patient's pleural space.

There is a significant drawback in converting a device, such as the cardiotomy, from intraoperative use to post operative use. The removal of tubing from the barbed connectors, by design, is difficult at best. Ordinarily, the tubing is left on the connectors when the device is discarded in the operating room.

However, in this situation where the device is not discarded, certain tubing will have to be removed from certain barbed connectors. This removal typically requires cutting of the tubing at the connector, thereby increasing the risk of violating the sealing feature of the barbs, and/or personal injury. This is also difficult to accomplish while maintaining aseptic technique.

The significance of having quick disconnects is therefore known by those skilled in the art.

The invention is changed from a cardiotomy reservoir to an autotransfusion unit by disconnecting the PVC tubing lines used during surgery by means of the quick disconnectors. A chest drainage tube inserted into the patient's chest provides a chest drainage function. The chest drainage tube allows the autotransfusion unit to then flow fluid through a reservoir outlet connector to a volumetric infusion pump. It is transported with the patient as the patient is taken from the operating room. The volumetric infusion pump is in turn connected to a line to the patient for intravenous flow into the patient.

The invention specifically operates in the advantageous manner of not requiring a separate manometer or low vacuum regulator extrinsic to the unit. The invention merely requires a line to be extended from the normal hospital fixed vacuum system to the unit without the interface of a separate manometer or flow control device.

The cardiotomy autotransfusion/pleural drainage reservoir eliminates the need for dedicated pleural drainage devices as well as the requirement for a separate water manometer. It reduces the need for homologous blood and blood products while supporting the patient's hemodynamic stability without the intrusion of various interfacing components. One component alone, namely the unit of this invention, need be used.

The action of the invention helps to conserve the blood of the patient as well as minimize the risk of transfusion related infections and serves to return the patient's plasma and electrolytes.

The invention hereof is also extremely time efficient. This is a critical element during operations. As can be appreciated, the less time in any operation that is utilized, the less exposure the patient has to problems, particularly during open-heart surgery.

The invention also provides for respective bypass capability and numerous optional features with respect to the various inlets and overall relationship which it enjoys. This is in conjunction with its utilization both during the surgery and post-operatively. This in fact is accomplished through the ease of its hookup and utilization on a patient's bed without extra equipment such as manometers, and related support equipment.

SUMMARY OF THE INVENTION

In summation, this invention comprises a cardiotomy reservoir for use during surgery, and a pleural drainage autotransfusion system incorporating a vacuum regulator.

The invention incorporates an outer casing or shell having inlet connections at the top. The inlet connections can be for utilization in conjunction with cardiotomy drainage during surgery or for other functions during surgery. A chest drainage inlet is also incorporated at the top for functioning during the post operative procedures by draining a patient's pleural cavity area.

A vacuum regulating system incorporating a water seal and balanced column of water to provide a given and regulated vacuum is within the shell. The integration of the vacuum regulating function within the shell provides for an integrated and compact unit which does not require a separate manometer or vacuum regulator and an extrinsic water seal.

The entire unit can be utilized as the cardiotomy reservoir during the surgery with quick disconnect inlets. After the surgery the lines to the inlets are then disconnected. The inlets are sealed and a chest drainage line is then connected to the chest drainage inlet of the unit in connected relationship to the pleural cavity of the patient. After filling the water seal and manometer, the unit is then merely attached to a hospital vacuum source. The vacuum is then regulated by the integral water column of this invention. The pleural drainage function of the unit proceeds to provide for autotransfusion with appropriate vacuum pull and reinfusion of the patient's fluids during post operative procedures through a volumetric infusion pump.

BRIEF DESCRIPTION OF THE DRAWINGS

The invention will be more clearly understood by reference to the description below taken in conjunction with the accompanying drawings wherein.

DESCRIPTION OF THE PREFERRED EMBODIMENTS

Figure 1:
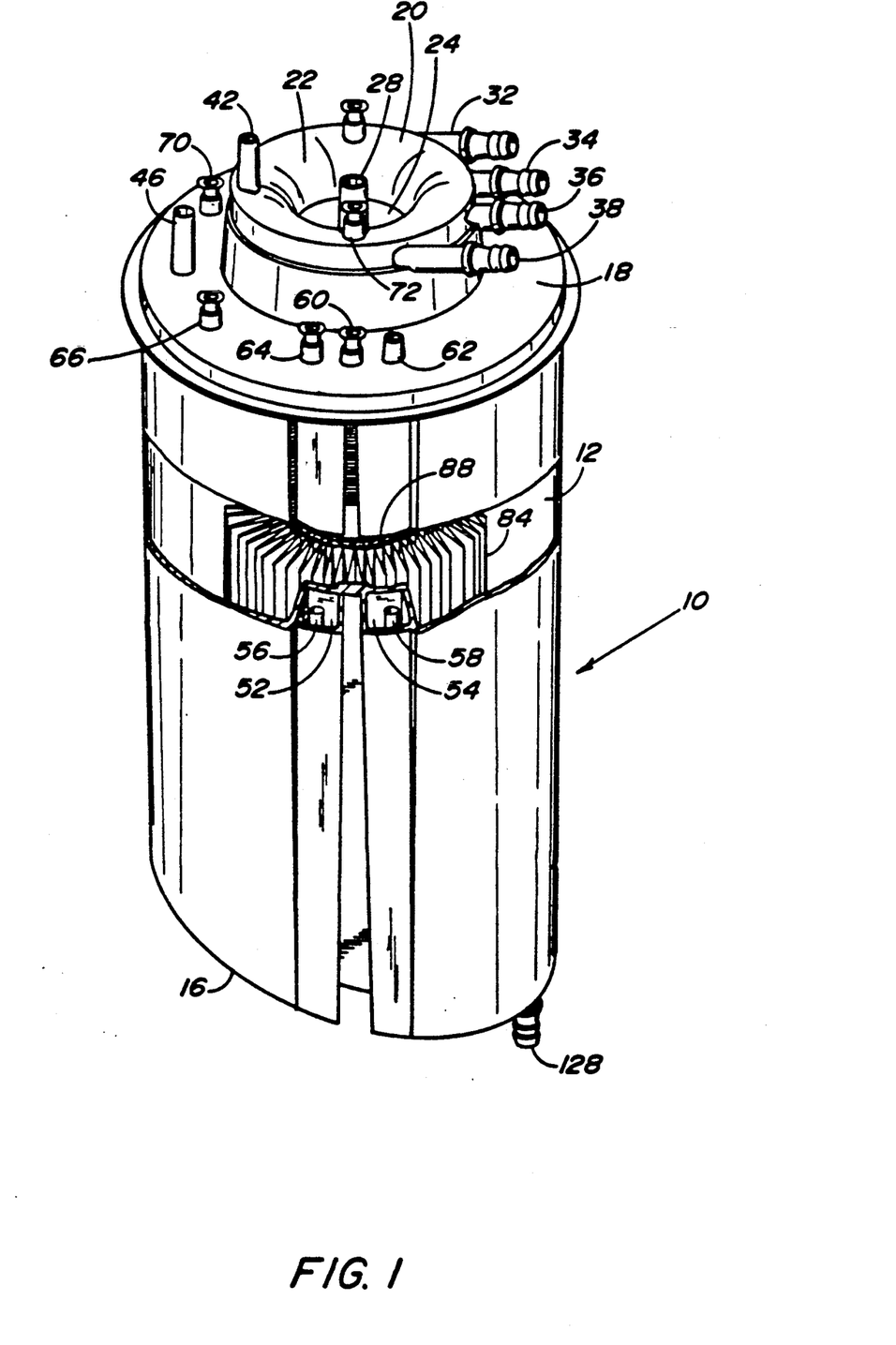
FIG. 1 shows a perspective view of this invention which has been cut away in part into approximately one third of the radius of the unit.

Looking at FIG. 1, a perspective view of the invention herein can be seen. The invention employs a walled cannister 10 having a reservoir 12 therein. The reservoir 12 is formed by an outer shell 14 in the form of a plastic cylindrical wall. The plastic cylindrical walled member can be molded from a single cylindrical molding with a base 16 formed therewith and a top or lid 18 that is sometimes referred to as a cap.

Figure 4:
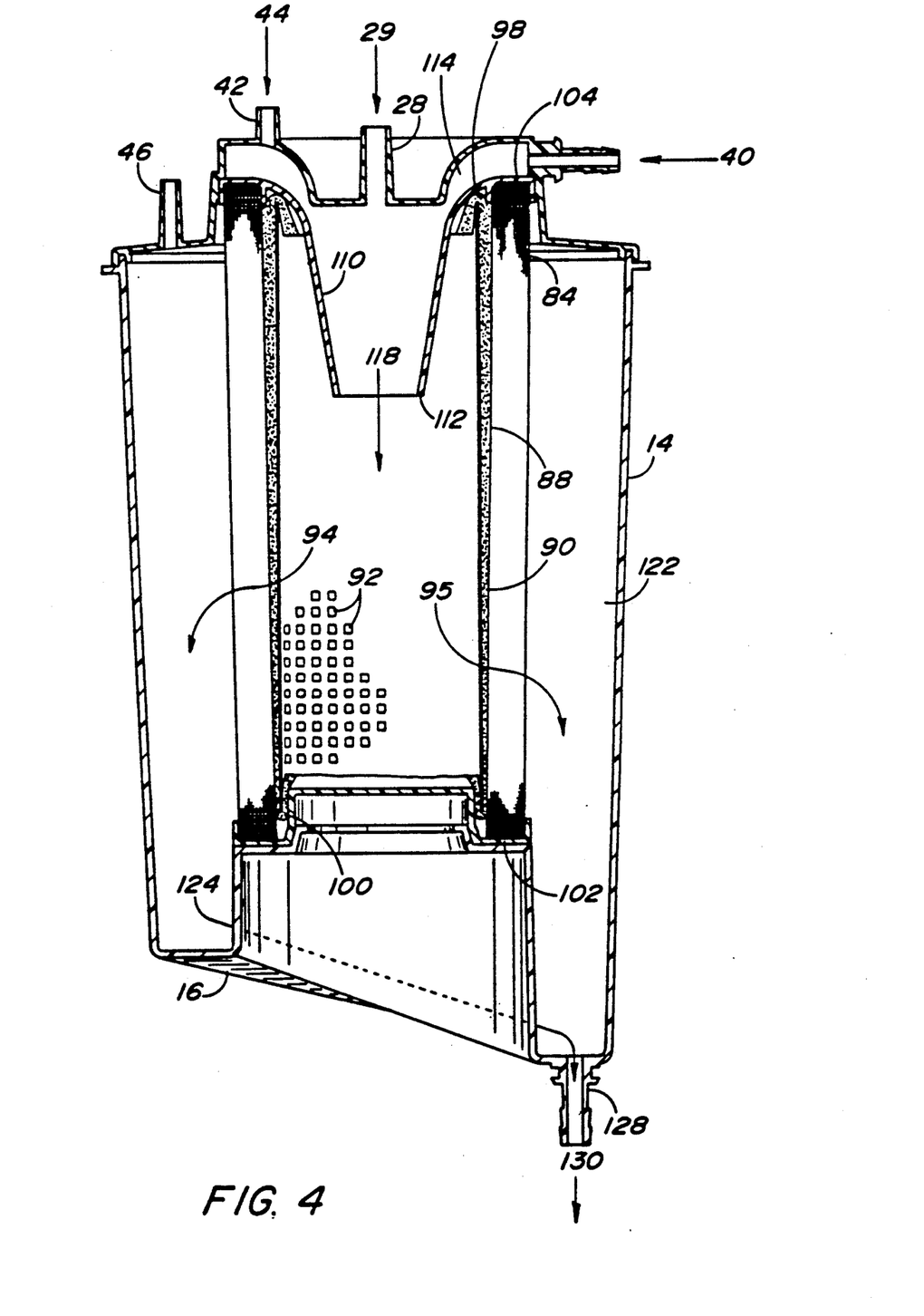
FIG. 4 shows a sectional view of the unit in the direction of lines 4—4 of FIG. 3.

The cap 18 is seated and sealed on the wall 14 of the cannister as will be seen in the sectional view of FIG. 4. The cap 18 has an upstanding circular boss 20 that has sloping walls 22 that slope downwardly to an inner disk surface 24. Within the inner disk surface a chest drainage or autotransfusion port 28 is provided. The autotransfusion port 28 is an elongated tubular member which stands upwardly in order to receive a chest drainage tube connected thereto.

The cap or top 18 has a number of fittings attached thereto which shall be detailed hereinafter. Four of these fittings can be seen in the form of barbed tubular ports 32, 34, 36 and 38. The ports 32 through 38 can be utilized for cardiotomy functions when the unit serves the function of a cardiotomy reservoir during surgery.

The ports 32 through 38 can provide passage of fluid from patients. The ports can also provide for convenience to introduce other fluids such as additional saline or banked blood into the unit. The four ports 32 through 38 are generally sealed with caps over their openings when not in use. They are also sealed during the time the unit is used for autotransfusion as will be seen hereinafter.

Arrow 40 of FIG. 4 has been shown in the direction of cardiotomy flow as well as any additive or other fluid flow into the unit.

The cap 18 can be further seen to have a port 42. Port 42 is a quick prime port. Fluid in the direction of arrow 44 can be introduced into the interior of the reservoir 12 to initiate the startup of the cardiotomy functions or other functions. Flow through port 42 is not absolutely necessary but is utilized in a quick priming manner by most surgical teams.

In order to help the unit displace air within it a vacuum/vent port 46 is included. This port 46 serves a dual purpose. The vacuum/vent 46 can be connected to wall suction to provide a negative pressure within the invention which is subsequently reflected through sucker tubing to the surgical field. Furthermore, as can be appreciated, during operations, the vacuum/vent can be opened to allow for venting of air, depending upon the particular functions that are being undertaken during the surgical procedure.

Within the side walls of the outer shell walls 14 is a semi-rectangular chamber 52 that comprises a water seal chamber and a second chamber 54 utilized for vacuum regulating. The water seal chamber has a tube 56 extending therethrough to within approximately one half inch of its base. The vacuum regulating chamber 54 also has tube 58 extending therethrough to approximately one half inch from the bottom of its base.

The two respective chambers 52 and 54 are filled to approximately two centimeters of water for the water seal chamber and twenty centimeters for the vacuum regulating chamber. These two chambers displace the traditional external regulator and water seal that are sometimes used. When a vacuum line is connected to them, as will be explained hereinafter, the system maintains a water seal through the chamber 52 and up to approximately twenty centimeters $H_2O$ of negative pressure through the vacuum regulating chamber 54.

Figure 2:
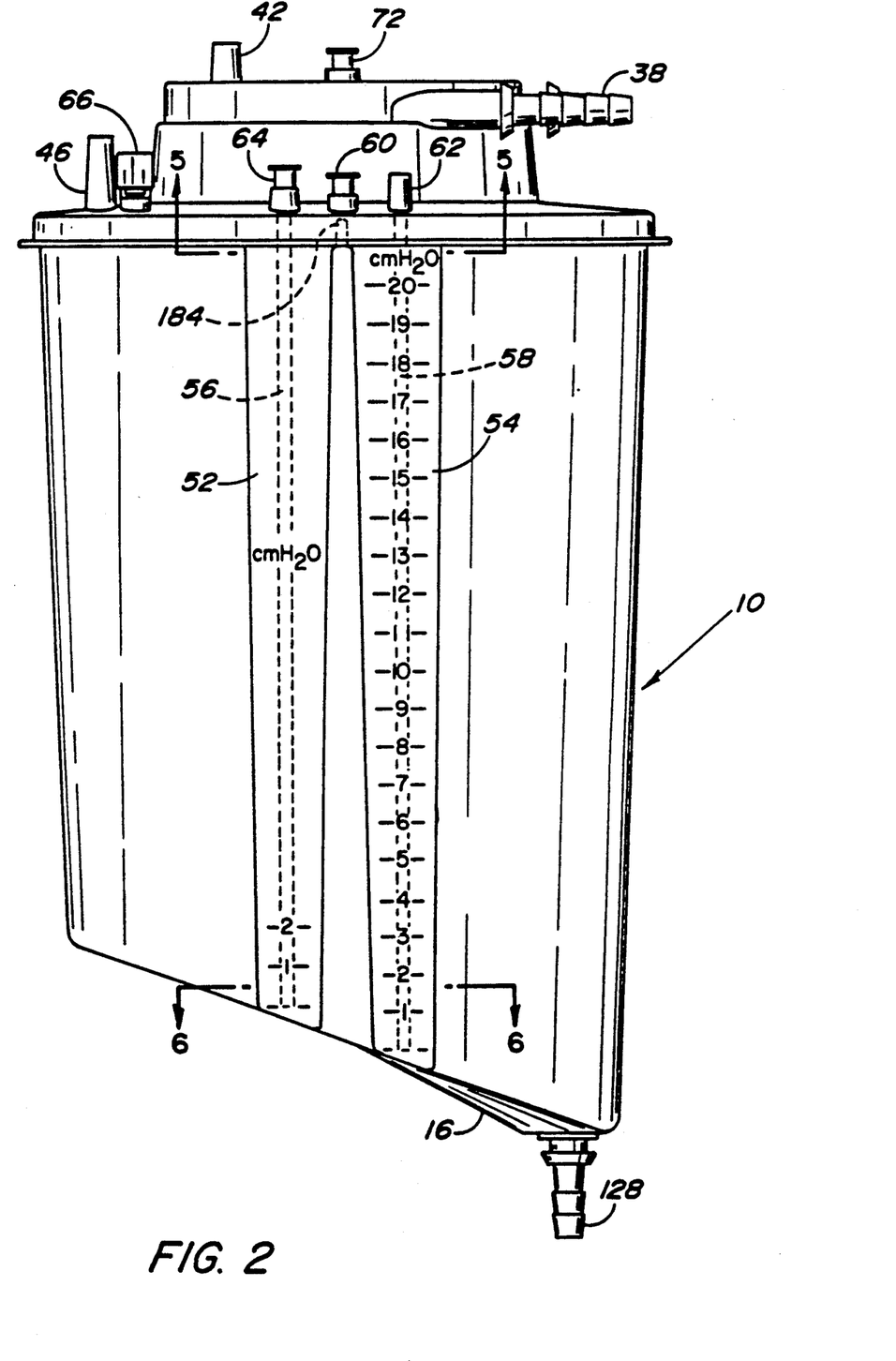
FIG. 2 shows a side elevation view of the unit of substantially the same frontal portion as seen in FIG. 1.

The vacuum connection is through a vacuum line hookup 60. This can be seen next to an atmospheric vent 62 that is connected to tube 58. A water seal reservoir communication port 64 is shown. The water seal connection port 64 is connected in a manner set forth hereinafter. It can be more readily seen in its operative connected form in FIG. 3 when the unit is to be used for pleural drainage/autotransfusion. The showing of FIGS. 1, 2 and 4 is when it is being used in the form of a cardiotomy reservoir.

Figure 3:
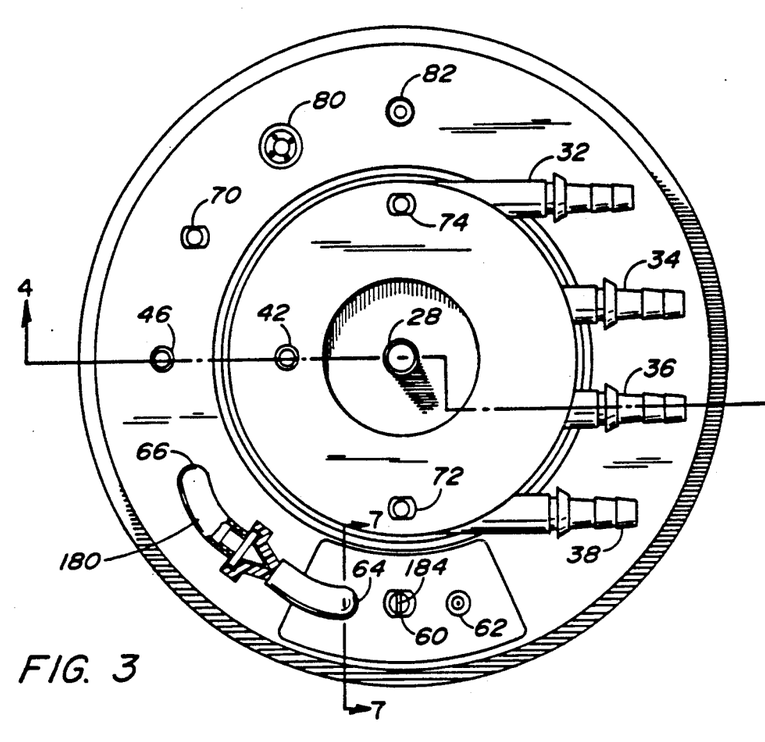
FIG. 3 shows a top plan view looking down on the unit of FIG. 1.

A through port 66 provides for the reservoir communication tube 180 that can be seen in FIG. 3. This shall be discussed hereinafter when the unit is changed from a cardiotomy reservoir to a pleural drainage/autotransfusion unit.

Oftentimes during both the surgery and post operatively, drugs are imparted to the patient. In order to do this, drug administration ports 66 and 70 are provided. The drug administration ports have luer lock fittings so that a syringe or other male luer fitting can be connected thereto.

The drug administration ports as shown by reference numeral 66 and 70 are outside of the filtration system. This can be exemplified further from the interior view of FIG. 4. This shows the fluid flow through the unit through the filter and then outside of it. The flow outside of the filter is in connected relationship to the drug administration ports 66 and 70.

A second series of luer lock connections for drug administration connect interiorly of the filter. These can be seen as luer lock drug administration ports 72 and 74. These luer lock drug administration ports allow for the introduction of drugs within the filter prior to the blood or other fluid passing therethrough.

The top 18 or cap is provided with valves to provide for release of positive and negative pressures. This is in part provided by combination positive and negative relief valves 80 shown on the top of the cap 18. A second valve, namely low pressure relief valve 82 in the form of an umbrella valve, is also provided. These respective valves allow for the bleeding and sustaining of pressure within the unit so that it will neither collapse nor expand inordinately. At the same time the valves have been set for the operating conditions necessary for both cardiotomy reservoir usage and autotransfusion usage. It is known to set these valves so that they can maintain the negative pressure of approximately minus twenty centimeters of $H_2O$ post-operatively.

The view in FIG. 1 shows the interior of reservoir 12 of the cannister having a pleated filter 84. The pleated filter 84 is shown in greater detail in the sectional view of FIG. 4. FIG. 4 specifically shows a sectional view of the pleated filter 84 and the interior support members thereof.

The pleated filter 84 as shown in FIGS. 1 and 4, can be formed from a ribbed polypropylene mesh and woven polyester screen. The pleated filter formation allows for extensive movement of fluid therethrough, while at the same time allowing a greater surface area for filtration than a mere cylindrical filtration member. The pleated filter serves for a greater through-put with less back pressure because of the broadened filtration surface area.

Again, looking at FIG. 1, it can be seen wherein a polyurethane foam 88 has been shown. This is also shown in FIG. 4 as the foam 88. Foam 88 is supported by means of a grid work 90. The grid work 90 has a number of openings 92 to allow for the passage of fluid therethrough in the direction of arrow 94.

The foam 88 is held at either end by means of being folded over the grid work 90. Grid 90 is a cylindrical member and secured at the top and the bottom of the grid work by being wrapped over corners 98 and 100. This holding in situ of the polyurethane foam secures it therein so that it can be moved inwardly and outwardly in a facile manner. The pleated filter is secured within a base groove 102 and an upper groove 104 by means of adhesive flowing into the pleated filter to secure it therein.

Flow in the direction of arrow 40 or flow through the autotransfusion drainage connection 28 in the direction of arrow 29 flows downwardly into the reservoir. It is guided by a funnel-shaped flow director 110 which is a conical member that has been truncated at surface 112. Fundamentally, the flow director 110 is a conical member having a belled-out portion 114 that circumscribes the interior and the upper wall as formed by the boss 20 or wall 22.

The flow direction as seen by arrow 29 through the flow director emerges at the lower surface 112 thereof in the direction of arrow 118. It then flows in the direction of arrow 94 and arrow 95 through the filtration unit. The flow arrives in the outer area of the cannister 122 and is allowed to flow downwardly in the direction of arrow 124. The base 16 being sloped in the direction of outlet 128 delivers flow in the direction of arrow 130 therethrough. Connection 128 is a barbed type of connector, similar in configuration to ports 32 through 38 which can receive a tube such as a quick disconnect similar in configuration to 240. This serves to deliver flow in the cardiotomy reservoir mode to a device such as an oxygenator or to transport fluid flow back to the patient through an infusion pump.

Figure 7:
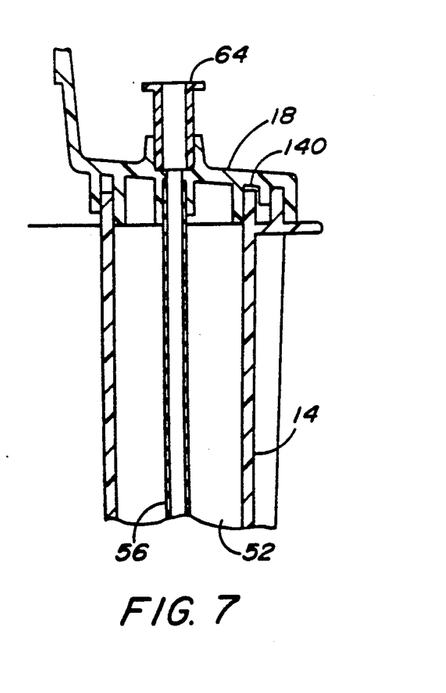
FIG. 7 shows a sectional view of the water seal as seen in the direction of lines 7—7 of FIG. 3.

The cap or top 18 is secured to the side walls or shell 14 of the reservoir by means of a tongue and groove or flange orientation. This can be seen in greater detail in FIG. 7. FIG. 7, although a sectional view in the direction of lines 7—7 of FIG. 3, details the water seal connection but nevertheless shows the cap 18 sealed at a tongue and groove connection 140. It should be understood that FIG. 7 shows in great measure the water seal rectangular chamber. In particular, rectangular water seal chamber 52 having tube 56 is shown in greater detail with the cap 18 sealed thereover. The cap 18 in the area outside of the water seal tube or chamber 52 and vacuum regulating chamber 54 normally merely relies upon the wall 14 forming a tongue to seal in a groove equivalent to tongue and groove portion 140. This is provided by the surrounding circumferential relationship between the wall 14 and the outer groove or flange of the cap 18.

In reference to the features of FIG. 7, it should be understood that the water seal connection 64 is shown in its upstanding position in FIG. 7 and is connected through the cap 18 to tube 56.

Looking more particularly at FIG. 2, it will be seen wherein the fittings that have been previously described, are shown. The showing of FIG. 2 includes a dotted showing of the water seal tube 56 within the chamber 52 and the vacuum regulating tube 58 within the chamber 54.

The two respective chambers or cavities 52 and 54 have water therein. The chamber 52 has water to approximately two centimeters in height and chamber 54 has water to approximately twenty centimeters in height.

These two respective chambers 52 and 54 function with the pleural drainage/autotransfusion portion of this invention in a manner to be described. Specifically, the atmospheric port 62 provides for the vacuum regulation. Port 60 provides for the vacuum hookup to a standard vacuum connection within a hospital bed area. Port 64 is a luer lock fitting that can be connected to through port 66 when it is uncapped. This connection is performed in the pleural drainage/autotransfusion mode by taking a piece of tubing, namely the communication tube 180 shown in FIG. 3, and interconnecting port 64 with port 66. The end result is a U-shaped connection that can be referred to as a pleural drainage/autotransfusion hookup between the respective ports 64 and 66. The communication tube 180 has a duck billed valve 181 with an elastomeric one way flap 183 that assures vacuum being drawn toward the chambers 52 and 54.

The quick prime port 42 is shown and is utilized in both the cardiotomy and autotranfusion functions.

A baffle connected to the vacuum hookup, namely the baffle 184 has been shown in dotted configuration in FIG. 2. This baffle divides the space between chambers 52 and 54. This can be more clearly seen in FIG. 5. The baffle can also be seen in FIG. 3 looking downwardly through the opening thereof. In particular, the baffle 184 is shown looking down through the openings 60 wherein the baffle divides the respective chambers 52 and 54.

Figure 5:
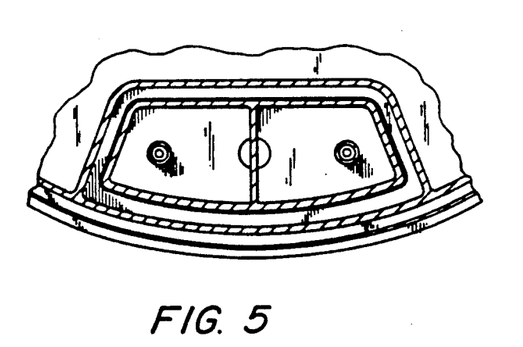
FIG. 5 shows a sectional view as seen in the direction of lines 5—5 of FIG. 2 showing the shared vacuum line between the water seal chamber and the vacuum regulating chamber of this invention.
Figure 6:
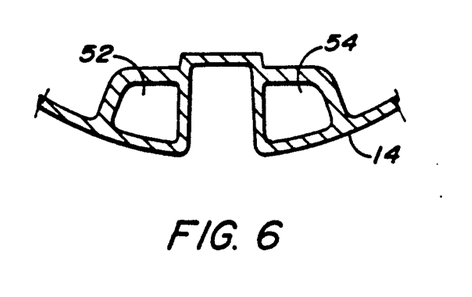
FIG. 6 shows a sectional view in the direction of lines 6—6 of FIG. 2.

Looking more specifically at FIG. 5 which is sectioned along lines 5—5 of FIG. 2, the ports 62 and 64 are seen. The vacuum hookup port 60 is shown with the baffle 184 therebetween. The baffle merely divides the two chambers 52 and 54, namely the respective water seal and vacuum regulation chambers. Vacuum provided through the port 60 is allowed to enter the chambers 52 and 54 and draw down thereupon to create the regulating function through the atmospheric port 62.

Any suitable type of baffle 184 can be arranged between the two respective chambers 52 and 54. The one requirement is that a vacuum must be established, with an appropriate water seal and a vent such as vent 62 to provide the regulated twenty centimeters of $H_2O$ vacuum.

For reasons known to those skilled in the art, a negative pressure is required in the pleural-mediastinal area. When the device is to be used as a pleural drainage/autotransfusion unit, it draws liquid and air from a patient's pleural or chest cavity area, thereby creating that negative pressure. In order to establish this negative pressure a vacuum is drawn through 60 which communicates with reservoir 12 and allows the withdrawal of fluids from the patient's chest area through port 28. The upper pressure of the vacuum at port 60 provided by the hospital vacuum line is in excess of twenty centimeters of $H_2O$. This causes the water column to be pulled down through tube 58 in chamber 58. This tube 58 communicates with atmospheric vent port 62, allowing air to be drawn in. The column of fluid in tube 54 regulates the negative pressure obtained in the patient's chest cavity. As the fluid is pulled down, it causes a bubbling at the base of the tube 58 within the chamber 54. The bubbling continues inasmuch as the atmospheric vent 62 allows for continued pull therethrough while at the same time maintaining a vacuum of up to twenty centimeters of $H_2O$.

The vacuum being drawn through the line 180 from port 66 within the interior of the entire chamber allows for constant pull through port 28 of up to twenty centimeters of $H_2O$. This is due to the fact that the vacuum provided within the chamber 52 is transmitted from port 64 through port 66 to the interior of the cannister 16. This maintains the negative pressure through port 28. In order to preclude atmospheric air and allow for a continuous vacuum, chamber 52 provides a water seal. The water seal allows for the vacuum drawn through port 64 down through tube 66 to be maintained with approximately two centimeters of water overlying tube 66.

Fluid drawn through the connection port 28 from the patient's plueral area, flows into this autotransfusion chest drainage inlet and down through the flow director 110. It is then allowed to flow through a filter that is provided by the filtration means previously referred to. The flow is allowed to flow directly and downwardly through outlet 128. The fluid from the outlet 128 can then be pumped by a volumetric infusion pump back to the patient through an intervenous connection.

The net result is to provide for a pleural drainage/autotransfusion unit and cardiotomy reservoir in combination with a vacuum regulator and water seal system.

When the unit is being used as a cardiotomy reservoir, lines 32 through 38 are in use at least as to one of the lines. Tube 180 does not interconnect ports 64 and 66. Port 64 is sealed with a luer lock fitting. When the device is to be used as an autotransfusion unit, the luer lock fitting is removed from port 64. Tube 180 is inserted thereover to provide for the vacuum communication to the reservoir 12.

After the surgery the cardiotomy reservoir is no longer needed and the patient is to be taken off the cardiotomy reservoir and reconnected to it as a pleural drainage/autotransfusion unit, previous systems could not be readily disconnected. Thus, it has been known to cut and clamp tubes connected to inlet ports 32 through 38. It is necessary of course for ports 32 through 38 to be appropriately sealed. This can be by means of a cap or fitting or other means to secure them in tightened relationship to provide the vacuum necessary within the chamber of the container or vessel.

Figure 8:
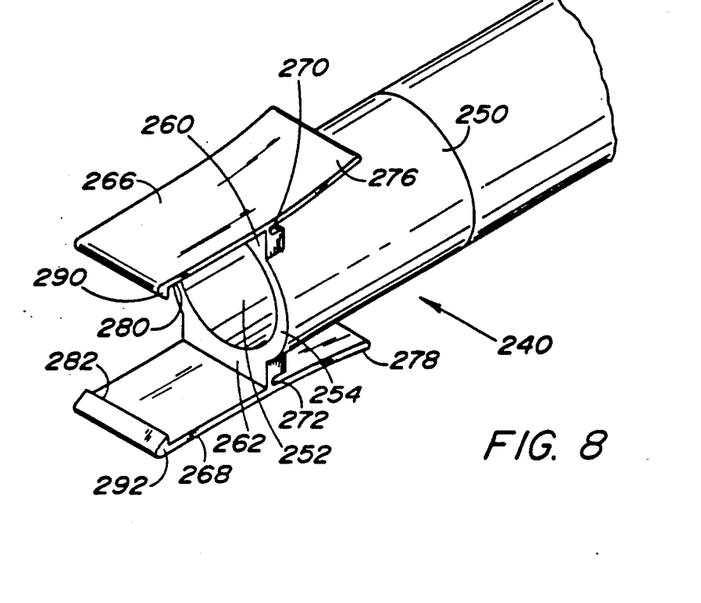
FIG. 8 shows a perspective view of the quick disconnect clamp and tube assembly.
Figure 9:
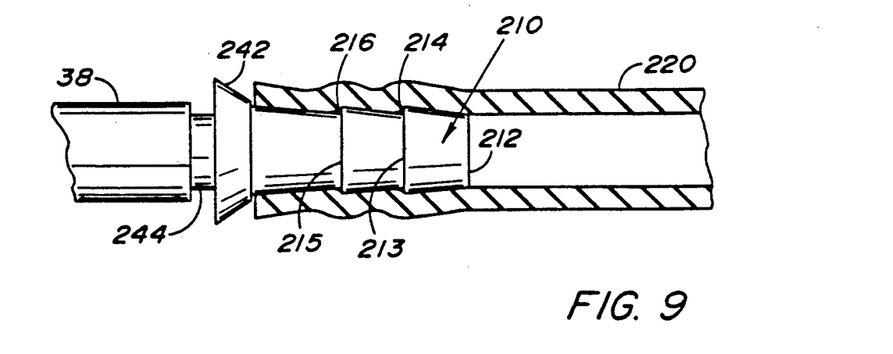
FIG. 9 shows a sectional view of a tube without the quick disconnect clamp on the barbed fitting portion of the quick disconnect barbed connector.
Figure 10:
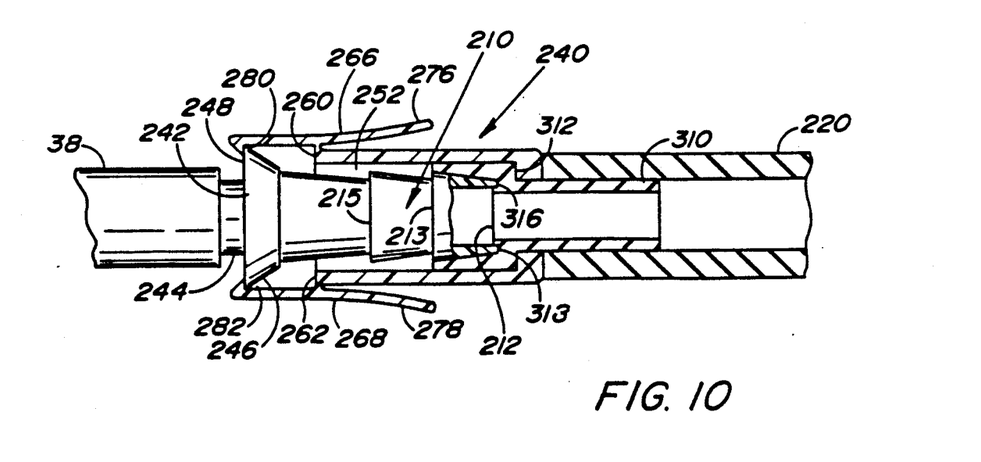
FIG. 10 shows a mid-line sectional view of the quick disconnect clamp assembly as seen in FIG. 8 when connected to a quick disconnect barbed connector such as that shown in FIG. 9.

The invention hereof enhances the connection and disconnection of lines that are connected to ports 32 through 38 during the operation by means of the quick disconnect device shown in FIGS. 8, 9 and 10.

In FIGS. 9 and 10, an exemplary port, such as ports 32 through 38 is shown. This has been shown as port 38 in FIGS. 9 and 10. Port 38, as in the case of ports 32, 34 and 36 has a barbed connector 210 which has been shown with an inlet 212 and barbs 214 and 216.

Generally, when barbs 214 and 216 engage the soft PVC tubing, the tube cannot be removed thereover. This is because of the fact that the PVC tubing shown as tube 220 flows by plastic deformation or creep into the respective low points of the barbs and cannot be withdrawn over the shoulders in adjacent relationship thereto. By not being able to be withdrawn over the shoulders of the barbs, the previously mentioned inappropriate removal of the tubes 220 is required.

The showing of FIG. 9 consists fundamentally of a prior art showing the way barbs engage tubing 220. This has been most unsatisfactory. The inventor hereof has invented a quick disconnect element for the entire invention to enhance the conversion of a cardiotomy to a pleural drainage/autotransfusion unit after the surgical procedure. However, as will be seen, this is significantly different from a prior invention set forth in U.S. Pat. No. 4,009,720 dated Mar. 1, 1977.

It should also be recognized the FIG. 9 shows that tubing 220 can be used alternately with the quick disconnect assembly 240 of FIG. 8. This is of significant importance as it allows the user to choose between the quick disconnect and the standard soft PVC tubing without sacrificing convenience.

The quick disconnect of this invention or fitting as shown in FIGS. 8 through 10 provide a plastic spring loaded tang member 240. The spring loaded tang member 240 is adapted for seating over the polycarbonate barbs and for connection to an angular collar 242. The angular collar 242 has a space 244 interfacing it with the polycarbonate tube 38. The flange 242 has a sloping surface 246 and a generally flat surface 248 which is a surface generally normal to the axis of tube 38. The surface 248 can be of any character, texture or angle so long as it engages the tanged device as set forth hereinafter, namely tanged device 240. In other words, it can slope toward the tube 48 or back slightly, so long as it engages the tangs of member 240. It can also be formed of any other suitable configuration, such as a spline or flange to receive the tangs of member 240.

Looking at quick disconnect 240, it can be seen that it is formed of a resilient plastic outer tubular member 250. The outer tubular member 250 has an opening 252 therethrough. The opening 252 is such wherein it can receive the outer dimensions of the barbs of members 32 through 38. The tubular portion 250 extends to a surface 254 surrounding the opening 252. Adjacent the opening 252 are two respective shoulders 260 and 262. The shoulders 260 and 262 extend upwardly to resilient levers 266 and 268. The resilient levers 266 and 268 are connected to the shoulders 260 and 262 respectively by means of webs 270 and 272.

The webs 270 and 272 can be of any suitable configuration to allow for the levers 266 and 268 to move backwardly and forwardly. Levers 266 and 268 comprise hand or finger operating portions 276 and 278. The hand or finger portions 276 and 278 allow for a depression thereof, thereby opening jaws 280 and 282. Jaws 280 and 282 terminate in barbs, tangs, or angular portions 290 and 292. The barbs 290 and 292 have surfaces adjacent the interior of the jaws which engage the upright or normal surface 248.

In order to release the members 266 and 268 from engagement, it is merely necessary to depress or squeeze together the handle portions 276 and 278, thereby allowing the member 240 to be withdrawn over the shoulders and surface 248.

Any suitable tang or tab arrangement 290 or 292 can be utilized as well as any other barbs or engaging means. The requirement is that the entirety should be capable of being removed through a simple opening of jaws adjacent to a receiving surface, such as surface 248.

In order to connect the member 240 to the polyvinyl (PVC) tube 220, an interconnecting stepped sleeve 310 is shown. The stepped sleeve has a shoulder 312 which expands upwardly against the interior shoulder of member 240. The stepped sleeve member 310 is bonded to the tube 220 by a solvent bond. It is only bonded at the tube 220 and is allowed to rotate freely in the space 252 of the member 240. This allows for radial orientation of the member 240 on the respective ports 32 through 38 in a facile manner.

The stepped shoulder insert is of a resilient material and allows the narrowed edge 316 of the barbed fitting to engage and depress the resilient material of the stepped shoulder insert 310 as shown at 318. As can be seen at 318, it is pressing into the resilient material in order to perform a sealing function.

It is the foregoing sealing function of the stepped insert 310 which allows for the functionality of the device so that a seal can be maintained. Prior art seals of this type and quick disconnects have not maintained the seal with barbed connector and a radially rotational member. Stepped member 310 is such wherein it engages a sharpened barbed member at the barbed portion 316 by being depressed as shown at 318 into the resilient media. Thus, it is believed that this sealing function and the flexible opening of the jaws allow for a dual tightened fixation that can be readily removed and at the same time maintain a seal between the ports 38 and the tube 220.

Based upon the foregoing advances of the art as specified herein, it is believed that this invention should be entitled to broad consideration and substantial breadth and scope applied to the following claims.

We claim:

1. A cardiotomy and body drainage-autotransfusion unit comprising a non-collapsible top and bottom joined by non-collapsible side walls which define at least one reservoir which receives body fluids directly within the walls comprising:

a plurality of ports within said unit including at least one drainage inlet port connected to said at least one body fluid reservoir to which a tube can be connected for receipt of draining fluids from the body of a patient, or for receipt of fluids for cardiotomy functions;

at least one outlet port connected to said unit which is in communication with said at least one body fluid reservoir for connection to a pump for the withdrawal of fluids from said at least one body fluid reservoir and delivery back to a patient in order to provide autotransfusion, or to a drain;

a vacuum regulating system within said non-collapsible unit occupying at least one of said at least one reservoir and including a vacuum regulating chamber and a liquid seal chamber;

at least one inlet port in communication with said liquid seal chamber and said vacuum regulating chamber for connection to a vacuum wherein said liquid seal chamber and said vacuum regulating chamber can be filled with liquid to a given level and, upon application of a vacuum, provide a controlled vacuum within said at least one body fluid reservoir for removal of body fluids from a patient under a controlled vacuum;

filtration means interposed between said inlet to said at least one body fluid reservoir and said outlet from said unit for filtration of body fluids received within said at least one body fluid reservoir;

an elongated conduit within said liquid seal chamber;

connection means connected to said elongated conduit;

a through port with connection means in communication with said body fluid reservoir adapted for connection to said connection means on said elongated conduit within said liquid seal chamber;

connection means in communication with said liquid seal chamber and said vacuum regulation chamber for applying a vacuum thereto; and, a baffle between said vacuum regulating chamber and said liquid seal chamber having an opening to allow a vacuum to be applied simultaneously to said vacuum regulating chamber and said liquid seal chamber.

2. A combination cardiotomy reservoir and body drainage-autotransfusion unit having a body fluid reservoir integrally formed within said unit with a vacuum regulating system therein comprising:

a non-collapsible canister having an outer shell with a body fluid reservoir therein;

a bottom portion to said outer shell;

a cap overlying said outer shell;

at least one inlet port means for introducing body fluid drainage into said body fluid reservoir to provide for autotransfusion and to provide cardiotomy functions;

at least one outlet port means disposed within the bottom of said reservoir for the removal of fluids;

filtration means interposed within said reservoir between said body drainage inlet port means and said outlet port means for said body fluid reservoir;

an elongated vacuum regulating chamber within said canister in adjacent relationship to said body fluid reservoir but separated therefrom by a wall from internal portions of said reservoir;

a conduit within said elongated vacuum regulating chamber extending toward the bottom of said chamber having an atmospheric vent connected thereto;

a vacuum connection to said elongated vacuum regulating chamber;

a means for connecting said elongated vacuum regulating chamber to the interior of said reservoir to maintain a vacuum in said chamber during body fluid drainage/autotransfusion usage, said vacuum being equivalent to a column of liquid within the elongated chamber; and, a liquid seal chamber within said canister in adjacent relationship to said body fluid reservoir but separated therefrom by a wall from the internal portions of said reservoir and which interconnects said vacuum regulating chamber with said reservoir.

3. The combination unit as claimed in claim 2 wherein said liquid seal chamber further comprises;

an elongated liquid seal chamber;

a conduit within said elongated liquid seal chamber connected at one end to said means for connecting said elongated vacuum regulating chamber to said body fluid reservoir; and, means for providing a common vacuum between said vacuum regulating chamber and said liquid seal chamber.

4. The combination unit as claimed in claim 3 wherein said liquid seal chamber and said vacuum regulating chamber utilize water as the liquid.

5. The combination as claimed in claim 3 wherein said liquid seal chamber interconnects said vacuum regulating chamber with the interior of said reservoir by means of a tubular member having two ends, one end being connected to one of said port means of said body fluid reservoir and the other end being connected to said conduit within said liquid seal chamber.

6. The combination unit as claimed in claim 5 further comprising:

markings on said vacuum regulating chamber to show the liquid column within said vacuum regulation chamber.

7. The combination unit as claimed in claim 2 wherein:

said cap has a plurality of ports for cardiotomy usage and to provide functions during operative procedures including the addition of drugs and other fluids into said reservoir.

8. The combination unit as claimed in claim 7 wherein:

said inlet and outlet ports have connection means which are adapted for quick connect and disconnect fittings.

9. The combination unit as claimed in claim 2 further comprising:

foam blood defoaming means interposed between said body drainage inlet port means and said outlet port means for said body fluid reservoir.

10. The combination unit as claimed in claim 9 wherein said filtration means comprise:

a support grid work;

said foam supported on said grid work; and, a pleated filter overlying said foam.

11. The combination unit as claimed in claimed 10 further comprising:

a baffle between said elongated vacuum regulating chamber and said liquid seal chamber that allows fluid pressure to extend there between for providing vacuum through a common vacuum port to each one respectively.

12. A combination unit as claimed in claim 10 further comprising:

a quick prime port connected to said body fluid reservoir.

13. A combination unit as claimed in claim 2 wherein said bottom portion of said outer shell comprises the bottom portion of said body fluid reservoir and is angled downwardly toward said outlet port disposed within the bottom of said reservoir.

14. A combination cardiotomy reservoir and body drainage-autotransfusion unit having a body fluid reservoir integrally formed within said unit with a vacuum regulating system therein comprising:

a non-collapsible canister having an outer shell with a body fluid reservoir therein;

a bottom portion to said outer shell;

a cap overlying said outer shell;

at least one inlet port means for introducing body fluid drainage into said body fluid reservoir to provide for autotransfusion;

at least one outlet port means disposed within the bottom of said reservoir for the removal of fluids;

at least one second inlet port means connected to said body fluid reservoir to provide a cardiotomy function;

filtration means interposed within said reservoir between said body drainage inlet port means and said outlet port means for said body fluid reservoir which comprises a support means, foam blood defoaming means supported on said support means, and a pleated filter;

a flow director extending into said body fluid reservoir within said filter;

means for connecting said body drainage inlet port and said cardiotomy ports with said flow director;

an elongated vacuum regulating chamber within said canister in adjacent relationship to said body fluid reservoir but separated therefrom by a wall from internal portions of said reservoir;

a conduit within said elongated vacuum regulating chamber extending toward the bottom of said chamber having an atmospheric vent connected thereto;

a vacuum connection to said elongated vacuum regulating chamber;

a means for connecting said elongated vacuum regulating chamber to the interior of said reservoir to maintain a vacuum in said chamber during body fluid drainage/autotransfusion usage, said vacuum being equivalent to a column of liquid within the elongated chamber; and, a liquid seal chamber within said canister in adjacent relationship to said body fluid reservoir but separated therefrom by a wall from the internal portions of said reservoir and which interconnects said vacuum regulating chamber with said reservoir.

15. The combination unit as claimed in claim 14 further comprising:

cardiotomy ports having connection means fittings adapted for quick connect and disconnect.

16. A method of providing cardiotomy and autotransfusion functions respectively during and after an operating procedure comprising:

providing a single vessel formed of a non-collapsible material which has a body fluid reservoir, a filter, and vacuum regulating means therein;

withdrawing body fluid from a patient during an operating procedure;

delivering said body fluid to said body fluid reservoir through the filter in said reservoir;

withdrawing said body fluid from said reservoir;

delivering said body fluid back to a patient during said operating procedure;

after said operating procedure, discontinuing withdrawing fluid from a patient and discontinuing delivering fluid to a patient;

connecting said reservoir to a vacuum source through said vacuum regulating means;

withdrawing fluid from a patient during an autotransfusion procedure by said regulated vacuum drawing body fluid into said body fluid reservoir;

withdrawing said body fluid from said body fluid reservoir by a positive displacement pump; and, pumping said body fluid from said positive displacement pump to a patient to provide autotransfusion after cardiotomy functions wherein said cardiotomy function and autotransfusion are performed through the same unit.

* * * * *